United States Patent
Giampapa

Patent Number: 5,421,831
Date of Patent: Jun. 6, 1995

[54] SUB-MALAR FACIAL IMPLANT

[76] Inventor: Vincent C. Giampapa, 89 Valley Rd., Montclair, N.J. 07042

[21] Appl. No.: 913,011

[22] Filed: Jul. 14, 1992

Related U.S. Application Data

[63] Continuation-in-part of Ser. No. 688,130, Apr. 19, 1991, abandoned.

[51] Int. Cl.⁶ ............................................... A61F 2/28
[52] U.S. Cl. .......................................... 623/16; 623/11
[58] Field of Search ....................... 623/8, 10, 11, 12, 16

[56] References Cited

U.S. PATENT DOCUMENTS

| | | | |
|---|---|---|---|
| D. 290,877 | 7/1987 | Giampapa et al. | 623/16 |
| D. 290,878 | 7/1987 | Giampapa et al. | 623/16 |
| D. 290,879 | 7/1987 | Giampapa et al. | 623/16 |
| 3,720,959 | 3/1973 | Hahn | 623/16 |
| 4,215,438 | 8/1980 | Pappas | 623/16 |
| 4,563,778 | 1/1986 | Roche et al. | 623/16 |
| 4,566,138 | 1/1986 | Lewis et al. | 623/16 |
| 4,636,216 | 1/1987 | Tatum | 623/16 |
| 4,684,370 | 8/1987 | Barrett | 623/16 |
| 4,728,330 | 3/1988 | Comparetto | 623/16 |
| 4,731,082 | 3/1988 | Giunta | 623/10 |
| 4,828,495 | 5/1989 | Bell et al. | 623/16 |
| 4,888,018 | 12/1989 | Giampapa | 623/16 |
| 4,955,395 | 9/1990 | Manders | 623/8 |
| 4,969,901 | 11/1990 | Binder | 623/16 |
| 4,990,160 | 2/1991 | Terino | 623/16 |
| 5,030,232 | 7/1991 | Pham | 623/10 |
| 5,067,962 | 11/1991 | Campbell et al. | 623/13 |
| 5,071,433 | 12/1991 | Naestoft et al. | 623/8 |
| 5,108,447 | 4/1992 | Zeiler et al. | 623/16 |
| 5,139,497 | 8/1992 | Tilghman et al. | 623/16 |

Primary Examiner—David Isabella
Assistant Examiner—Gina M. Gualtieri
Attorney, Agent, or Firm—M. K. Silverman

[57] ABSTRACT

A facial implant for augmentation of the sub-malar region of the face includes a three dimensional body formed of a flexible tissue-compatible material having a convex front surface and a concave rear surface, such surfaces being substantially symmetrical about a plane of symmetry existing about midway between proximal and distal tips of the body, at which tips the convex and concave surfaces intersect. The body is also characterized by a thin proximal head portion consisting of upper and lower protrusions existing proximally with reducing thickness, a wider central portion, and a tail portion extending distally with reducing height and thickness to the distal tip of the body of the implant.

6 Claims, 3 Drawing Sheets

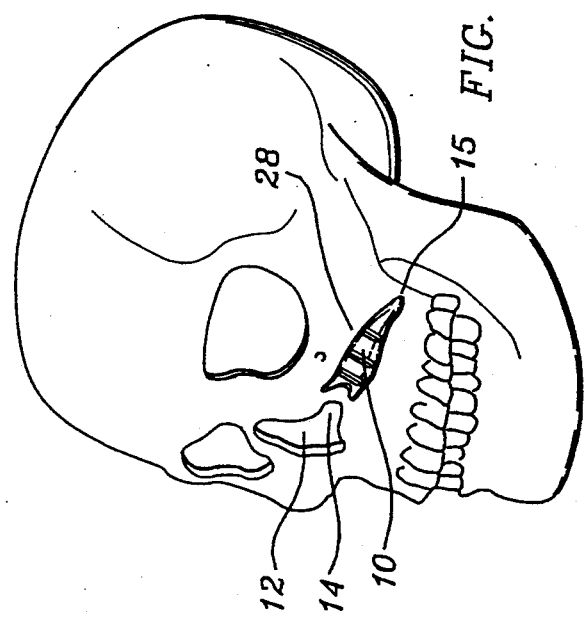
FIG. 3.
_Prior Art_

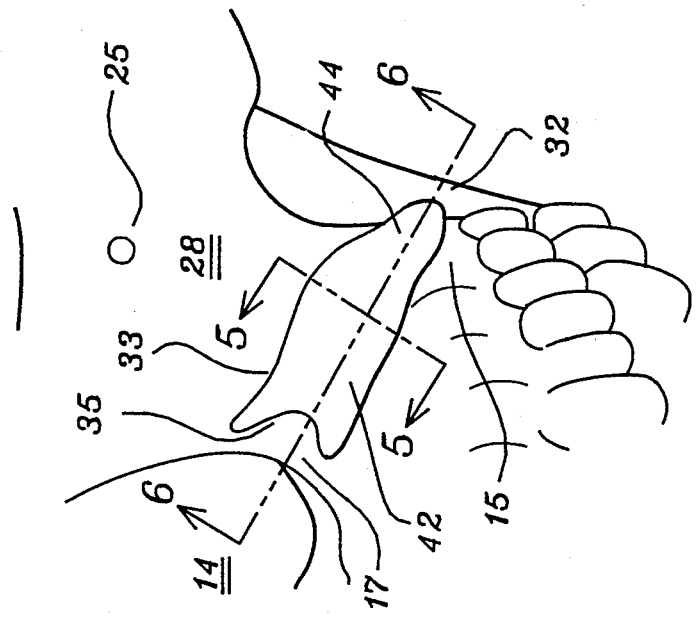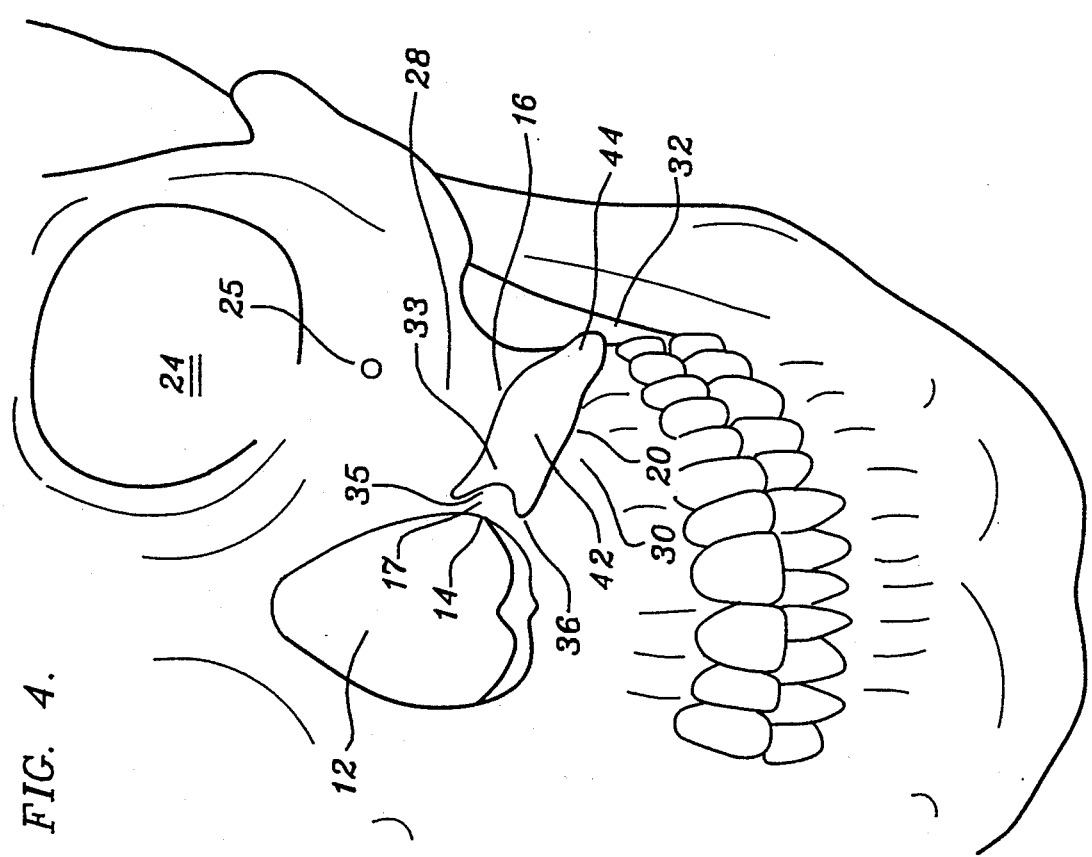

SUB-MALAR FACIAL IMPLANT

REFERENCE TO RELATED APPLICATION

This case is a continuation-in-part of application Ser. No. 07/688,130, filed Apr. 19, 1991, entitled Sub-Malar Implant, now abandoned.

BACKGROUND OF THE INVENTION

The present invention relates to the area of plastic surgery and, more particularly, to a facial implant usable in reconstructive and cosmetic surgery of the sub-malar region of the face, said implant usable, in addition to other uses, as a maxillary bone prosthesis.

Facial surgery involves the reconstruction of cutaneous tissue, particularly about the face, which is performed to correct defects resulting from either trauma, disease, or the normal marks of time. More particularly, facial plastic surgery, as commonly known today, is employed to improve the shape and contour of particular portion of the face. More particularly, this need is a consequence of the increased prominence of the nasal labial folds, which prominence occurs with the aging process. This phenomena is caused by attenuation of the so called SMAS fibers and surrounding supporting structures of the facial musculature which insert into the nasal labial fold at the level of the dermis. Also contributing to the prominence of the nasal labial folds is the lack of tone of the overlying facial skin, which also descends with the aging process. Finally, the fatty thickness of the skin and subcutaneous tissue in this area also atrophy as the aging process advances.

All of the above set forth conditions contribute to reduction in soft tissue thickness and a loss of tone of the skin in the nasal labial area of the face. This region is referred to by plastic surgeons as the central lower third of the face. The final result of all three of the above processes is that of a sunken, tired look around the mouth and above the upper lip area.

Historically, the above has been an extremely difficult problem to correct, even with state-of-the-art face-lifting procedures. Past corrective attempts have included SAMS plcication, deep plane rhytidectomy, direct excision of the overlying folds and multiple injection therapies of materials including otologous fat, silicone and collagen.

The instant invention resulted from the discovery that aesthetic improvement of the nasal labial folds can be accomplished by augmentation of the underlying bony structures in this area that is, of the nasal maxillary bone junctions. Such augmentation of this area operates to elevate the overlying SAMS fibers and subcutaneous tissues anteriorly. This procedure has the effecti of stretching the overlying subcutaneous skin or soft tissue as well as the overlying SAMS fibers by increasing the convex outer surface of the underlying bony skeleton with a resultant restoration of the fullness of the atrophied overlying subcutaneous tissues, this bringing about an overall more youthful look in this area.

In the prior art it is known to augment the human chin as is reflected in U.S. Pat. No. 4,344,191 (1982) to Wagner, and in my own U.S. Pat. No. 4,888,018 (1989).

Also, augmentation of the mid-facial maxilla, the mid-face zygoma and mid-face zygomatic arch, are known as is taught in my U.S. Pat. Nos. D.D. 890,877, 290,878, and 290,879.

Implants are also known which provides support to the orbital rim of the eye in the area of the zygomatic arch, as is taught in U.S. Pat. No. 4,790,849 (1988) to Terino, which implant is shown in the illustration of the prior art which is FIG. 1 of the Drawings. The teaching of said reference to Terino differs from that of the instant invention in that its utility is in connection with intraoral procedures, blepharophasty, and other procedures of the orbit and maxilla, whereas the instant invention, as set forth below, is concerned with procedures of an intraoral nature directed to surgery of the pyriform aperture and, as above described, of the nasal labial folds and nasal maxillary junction. Also, the underlying purpose of Terino is that of raising cheeks in the area of the zygomatic arch to counter the aging process in that area and, as such, is more related to my above reference U.S. Pat. No. D.D. 290,879 (1987) entitled Mid-Facial Zygomatic An Skeletal Implant. My instant invention has, as its purpose, not the augmentation of the cheeks but, rather, the elevation of subcutaneous tissues and muscles overlying the nasal labial fold area, including the SAMS fibers, and further, enhancement in the areas known as the levator labil superioris, the levator anguli otis, and the levator alae. In short, the purpose of the instant invention is to correct atrophication and thinning of subcutaneous tissue in the nasal labial fold area. Other art known to the inventor includes U.S. Pat. No. 4,969,901 (1990) to Binder entitled Plastic Surgery Implant. Binder, like Terino, is concerned with intraoral device. Further, the device of Binder is intended for use in the sub-malar area, technically known as the canine fossa. Its use requires suturing into a subcutaneous pocket therefore. The structure and method of Binder may be thought of as a different method and structure for achieving a number of the objectives which, in my opinion, are more effectively achieved by the method and structure of my inventive sub-malar facial implant as is set forth herein.

SUMMARY OF THE INVENTION

The present invention comprises a facial implant for augmentation of the sub-malar region thereof, the implant more particularly including a three dimensional body, formed of a flexible tissue-compatible material, having a convex front surface and a concave rear surface, said surfaces being substantially symmetrical about a plane of symmetry existing medially between proximal and distal tips of the body at which tips said convex and concave surfaces intersect. Said body further includes a thin proximal head portion consisting of upper and lower protrusions proportioned to approach the nasal maxillary junction, said protrusion extending proximally with reducing thickness. The body further includes a wider central portion and a tail portion extending distally with reducing height and thickness to said distal tip of the body. The body further combines a generally convex curved upper surface and a generally concave-curved lower surface when viewed from front to back.

It is an object of the present invention to provide a sub-malar implant that may be positioned at either side of the nose and above the upper lip, while covering the area abutting the pyriform aperture to thereby lessen the effects of aging including lines at either side of the nose and above the upper lip commonly referred to as naso-labial folds.

It is another object of the invention to provide a sub-malar implant that will support the mid cheek while reducing the visibility of lines and folds in the area of the pyriform aperture, thereby providing a more useful appearance after implantation of a left and right pair of sub-malar implants in accordance with the invention.

It is a further object to provide a facial implant for the augmentation of the facial skeleton in the region immediately abutting the pyriform aperture to thereby support tissue which is commonly impaired as a function of age.

A yet further object is the provision of a sub-malar implant that may be utilized either subcutaneously or subperiousteally.

The above and yet other object and advantage of the present invention will become apparent in the hereinafter set forth Brief Description of the Drawings, Detailed Description of the Invention, and the Claims appended herewith.

BRIEF DESCRIPTION OF THE DRAWINGS

FIG. 3 is a front elevational view of the facial skeleton showing the inventive implant positioned beneath the malar complex.

FIG. 4 is an enlarged front view of FIG. 3 showing the structure and orientation of the inventive facial implant.

FIG. 4A is an enlarged view of the implant region of FIG. 4.

DETAILED DESCRIPTION OF THE INVENTION

Figure 2:
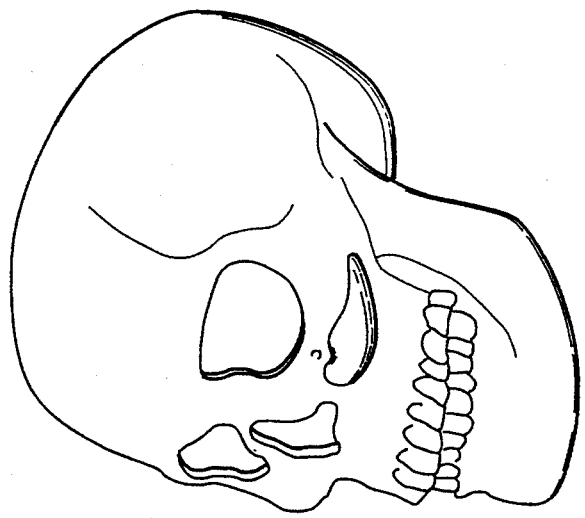
FIG. 2 is a side elevational view of a prior art facial implant in accordance with U.S. Pat. No. 4,969,901.
Figure 1:
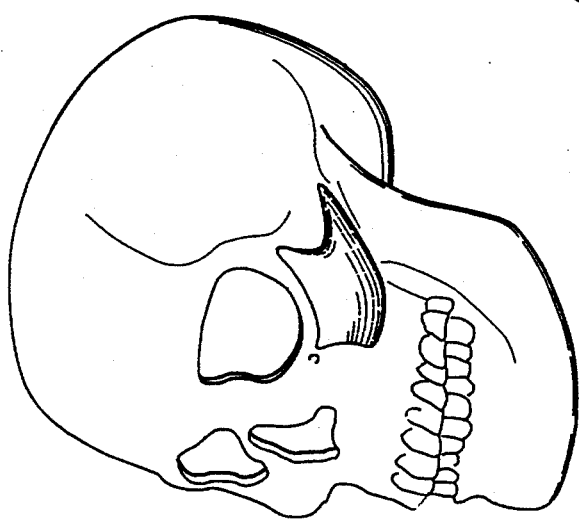
FIG. 1 is a side elevational view of a prior an facial implant according to U.S. Pat. No. 4,790,849.

There is, in the views of FIGS. 1 and 2, shown prior art facial implants for use in the facial area. More particularly, the prior art of Tefino, reflected in U.S. Pat. No. 4,790,849, relates to a structure concerned with support of the lower orbital rim in the area of the zygomatic arch to raise cheeks of the face and thereby decrease the appearance of aging caused by sagging in the zygomatic arch area. As such the prior an of FIG. 1 represents an adaptation of the design shown in my U.S. Pat. No. D.D. 290,879 (1987) entitled Mid-Facial Zygomatic Arch Skeletal Implant. As is more fully described above in the Background of the Invention, the prior art of Tefino is not concerned with the same anatomical area of the face as is my invention described herein.

With respect to the prior art implant shown in FIG. 2, this corresponding to the structure of Binder shown in U.S. Pat. No. 4,969,901, the position of the structure thereof is in an area known as the canine fossa. Its location is far from the pyriform aperture (more colloquially known as the nasal notch). As such, the structure of Binder does not focus directly upon the nasal maxillary junction or its role in the aging process.

With reference to the views of FIGS. 3, 4 and 4A, the inventive sub-malar implant 10 is seen to be positioned immediately outwardly of nose 12 and, particularly, immediately abutting the pyriform aperture 14. As may be seen, the position of the implant is defined by a line from a proximal head portion 33 which starts at pyriform aperture 14 and continues to a distal tip 32 which extends downwardly and laterally to the canine eminence 15 the orientation of the implant 10 (see FIGS. 5 and 6) is such that the upper edge 16 of rear surface 18 rests against the convex curve of the lowermost portion of the malar complex i.e., mid-cheek 28.

Figure 5:
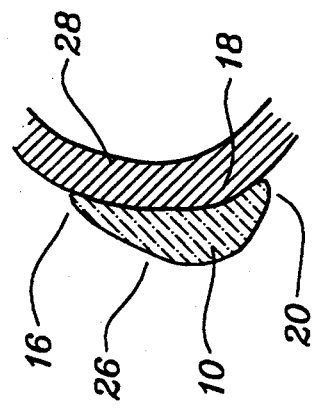
FIG. 5 is a cross-sectional view taken along Line 5—5 of FIG. 4A.
Figure 6:
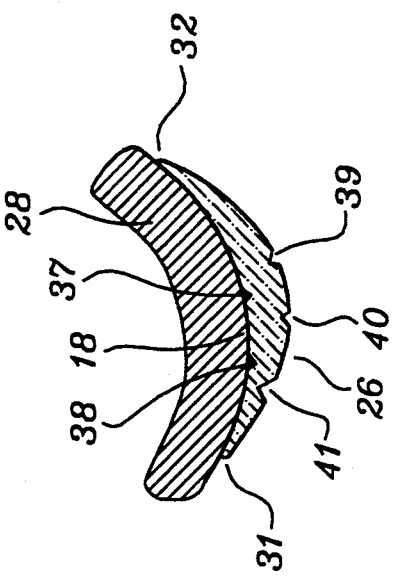
FIG. 6 is a cross-sectional view taken along Line 6—6 of FIG. 4A.

As may be further noted in the views of FIGS. 4 to 6, a lower-edge 20 of the implant extends to the area of the beginning of upper lip 30 of the patient, i.e., the canine eminence 15.

It is to be appreciated that infraorbital foramen 25 provides a passageway for several vessels and nerves to the cheek and upper lip. Physical contact with these vessels or nerves by any implant would result in discomfort and perhaps disabling symptoms in the immediate area and down to the upper lip and cheek, thereby affecting nerves passing through the pyraform aperture 14.

Accordingly, the design and placement of the implant 10 is to abut the pyraform aperture 14 while avoiding contact with the nerves and blood vessels that pass through the infraorbital foramen 25.

Figure 7:
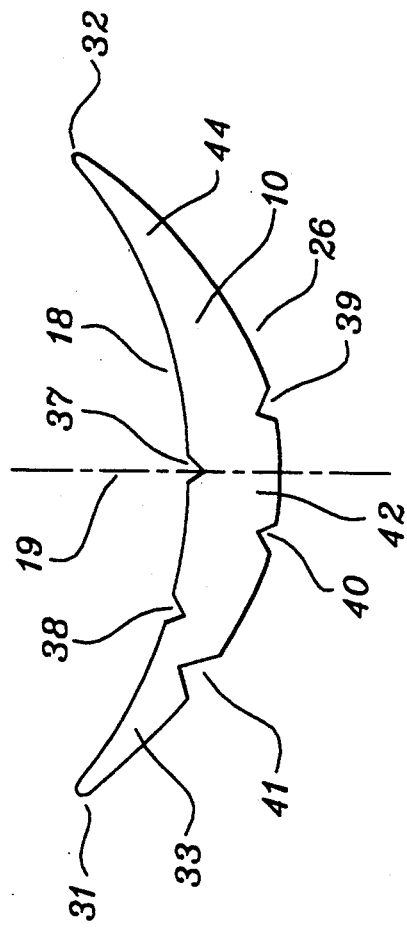
FIG. 7 is a top plan view of the implant.
Figure 8:
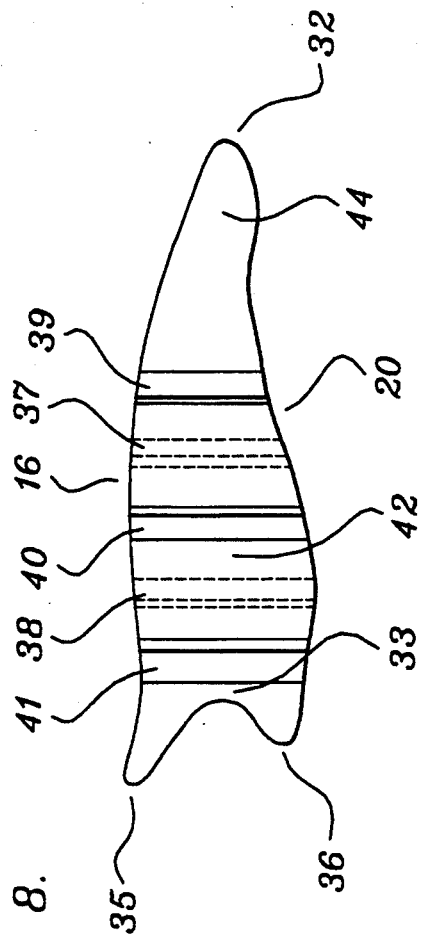
FIG. 8 is a front plan view thereof.

As may be noted in the cross-sectional views of FIGS. 5 and 6 and the plan views of FIGS. 7 and 8, the generalized geometry of the inventive implant is that of a three dimensional body 10 having a convex front surface 26 and a concave rear surface 18. Said curved surfaces are substantially symmetrical about a plane of symmetry 19 (see FIG. 7) which exists approximately midway between proximal tip 31 and a distal tip 32. It is noted that the convex and concave surfaces 18 and 26 respectively intersect at said tip 31 and 32. Tip 31 is termed the proximal tip because of its nearness to the pyraform aperture 14 (See FIG. 4).

The body of the implant 10 includes said proximal head portion 33 consisting of upper and lower protrusions 35 and 36 respectively which extend proximally toward aperture 14 with decreasing thickness in the direction of the aperture. As above noted, said respective upper and lower protrusions 35 and 36 are proportioned for engagement about the nasal maxillary junction 17 (see FIGS. 4 and 4A). The implant 10 also includes a wider central portion 42 (see FIG. 7) and a tail portion 44 extending distally with reducing height and thickness to said distal tip 32 of the implant body.

As may be seen in FIGS. 4 and 8, the implant body further defines a generally convex curved upper surface 16 and concave-curved lower surface 20, when viewed from front-to-back.

The implant itself is formed of a flexible tissue compatible material such as a medical-grade silicone plastic manufactured by Dow-Corning Company under the name of SILASTIC. Such implants may be manufactured in sizes of small, medium, large and extra large. Thus this range, the greatest length of the implant body will be 2.9 to 3.7 centimeters, the greatest vertical height from 1.2 to 1.4 centimeters and the greatest front to back width from 3 to 4 millimeters.

In the preferred embodiment the implant is provided with front and rear surface articulations which provide flexibility to the structure and superior conformance to implant subpefiosteal and subcutaneous locations which do not require the use of suturing, as is the case in the above referenced prior art to Binder. Such articulation, more particularly, include a central V-shaped articulations 37 (see FIGS. 7 and 8) located upon said concave rear surface 18 and upon said plane of symmetry 19. Therein the apex of the articulation is directed toward the front surface 26 of the implant body. There may additionally be provided a proximal V-shaped articulation 38 positioned upon the concave-rear surface 18 about midway between said plane of symmetry 19 and the proximal tip 31 of the implant. If articulations are placed upon the convex or outer surface 26, articulations 39 and 40 may be provided upon opposite sides of the plane of symmetry 19 as noted in FIG. 7. Further, a distal articulation 41 may be provided on surface 26 about midway between proximal tip 31 and said articulation 40. The above described regime of articulations 37 through 41 provide a customized flexibility, stability and generalized natural characteristic to the surgical results, whether used subcutaneously or subperiosteally. Such articulations also act to reduce the pressure transmitted to skin above the implant by absorbing tension therefrom, this decreasing the liklihood of implant erosion or extrusion.

With respect to the applicable surgical procedure, the patient is taken to a minor surgical area and placed in supine position. An infraorbital block is administered bilaterally. Pyraform apertures of the left and fight side of the nose are infiltrated with a twenty-five gauge needle to the depth of the nasal maxillary junction 17 immediately below the nasal labial folds. The pyraform aperture is prepped with BETADINE. After the appropriate time for anesthesia to take effect, a small stab incision is made in the pyraform aperture. Utilizing a blunt tipped dissecting scissors, a subperiosteal or subcutaneous pocket is made immediately below the nasal labial fold and above the periosteum. This conforms to the underlying nasal maxillary junction.

Upon completion of this pocket, the nasal aperture is spread with a speculum. The zonal implant of the instant invention is grasped with a long, straight clamp and placed directly into the pyraform aperture onto to the overlying bone below the nasal labial fold or in the subcutaneous tissue below the labial fold. Intraoral palpation is accomplished during both the dissection and placement of the implant to make certain that the pocket is not ascended too inferiorly and that the implant will not be palpable through the bupccal sulcus. Upon a completion of the placement of the implant, the pocket is irrigated with about 3 cc of BACITRACIN antibiotic solution and the incision is then closed with two interrupted sutures of 5-0 CHROMIC. The patient is then given oral antibiotics for five days post-operatively along with oral analgesics.

From the above results an immediate improvement in the fullness of the central lower third of the face and the nasal labial fold prominence is effected. The above procedure takes only about ten minutes to perform, and is easily accomplished under the above set forth local and block anesthesia.

With such ease of accomplishment of the above procedure, the more conventional techniques of injection of collagen, liquid silicone and other materials, with their attendant risks, can be avoided. Implants of the above described SILASTIC material are easily placed in location, either subcutaneously or subperiosteally, with minimal concern for infection. Utilizing the subnasal insertion route, which differs from the route of insertion of related prior art implants, a completely inconspicuous incision may be used and the area of interest may be easily approached. No vital anatomical structures are present in this deep plane dissection that might otherwise be a concern to the physician. Accordingly, a safe, rapid and effective procedure for face-lifting in the area of the nasal labial folds is accomplished.

Over twenty-five patients have been operated on bilaterally (both sides of the face) for restoration and improvement of the nasal labial fold area employing the above technique and implants.

It is therefore believed that the above procedure with the use of the inventive implant will add a new dimension in the correction of nasal labial folds which in the past have proved to be a very difficult area for plastic surgeons to operate upon.

Accordingly, while there has been shown and described the preferred embodiment of the invention certain changes may be made in the form and arrangement of the parts without departing from the underlying principles of this invention within the scope of the claims appended here.

Having thus described my invention what I claim as new, useful and non-obvious and, accordingly, secured by Letters Patent of the United States is:

1. A facial implant for augmentation of a sub-malar region, comprising:
   (a) a three-dimensional body having proximal and distal tips, formed of a flexible tissue compatible material having a convex front surface and a concave rear surface, said surfaces substantially symmetrical about a plane of symmetry existing medially between said proximal and distal tips of said body at which said convex and concave surfaces intersect, said body further having a bifurcated head portion extending From the proximal a central portion and a tail portion extending from the distal tip, the body being the widest at its proximal head portion and being tapered in height and thickness through the central portion to its distal tail portion.

2. The implant as recited in claim 1 in which said body further defines a generally convex curved upper surface.

3. The implant as recited in claim 2 in which the body further defines a generally concave-curved lower surface.

4. The implant as recited in claim 1, said body further having a central articulation upon said concave rear surface and at said plane of symmetry, an apex of said articulation directed toward said front surface of the body.

5. The implant as recited in claim 4, said body yet further having a proximal articulation on said concave rear surface positioned about midway between said plane of symmetry and said proximal tip of said head portion of the body.

6. The implant as recited in claim 5, yet further having respective distal and proximal articulations upon said convex front surface, one each of said articulations on opposite sides of said line of symmetry and about equal in distance therefrom, said proximal articulation located about midway, between said central and proximal rear surface articulations.

* * * * *